United States Patent
Vilser et al.

(10) Patent No.: US 11,272,838 B2
(45) Date of Patent: Mar. 15, 2022

(54) DEVICE AND METHOD FOR DETERMINING RETINAL BLOOD PRESSURE VALUES AND FOR MAPPING RETINAL BLOOD PRESSURE VALUES AND PERFUSION PRESSURE VALUES

(71) Applicant: Imedos Systems GmbH, Jena (DE)

(72) Inventors: Walthard Vilser, Rudolstadt (DE); Benedikt Krauss, Jena (DE); Thomas Riemer, Jena (DE)

(73) Assignee: IMEDOS SYSTEMS GMBH, Jena (DE)

( * ) Notice: Subject to any disclaimer, the term of this patent is extended or adjusted under 35 U.S.C. 154(b) by 529 days.

(21) Appl. No.: 16/043,922

(22) Filed: Jul. 24, 2018

(65) Prior Publication Data
US 2019/0298171 A1    Oct. 3, 2019

(30) Foreign Application Priority Data
Mar. 29, 2018   (DE) .................... 10 2018 107 622.3

(51) Int. Cl.
*A61B 3/16*   (2006.01)
*A61B 5/03*   (2006.01)
(Continued)

(52) U.S. Cl.
CPC .............. *A61B 3/16* (2013.01); *A61B 3/18* (2013.01); *A61B 5/031* (2013.01); *A61B 3/12* (2013.01);
(Continued)

(58) Field of Classification Search
None
See application file for complete search history.

(56) References Cited

U.S. PATENT DOCUMENTS 3,706,304 A * 12/1972 Sisler .................. A61B 5/02216
                                                600/489
4,281,662 A *  8/1981 Brent .................... A61B 5/021
                                                600/400
(Continued)

FOREIGN PATENT DOCUMENTS

DE         1055175         10/1959
DE         3511938 A1      10/1986
(Continued)

OTHER PUBLICATIONS

Tonometer. (2021). Retrieved Jul. 19, 2021, from www.merriam-webster.com (Year: 2021).*

(Continued)

*Primary Examiner* — Matthew Kremer
*Assistant Examiner* — Samuel C Kim
(74) *Attorney, Agent, or Firm* — Patentbar International PC

(57) ABSTRACT

The invention relates to a device and a method, by which the intraocular pressure in a patient's eye is changed by artificially applying a variable stimulation pressure causing, upon reaching specific intraocular pressure values, the presence of characteristic measurement criteria in the retina of the eye, which allow global and local retinal blood pressure values to be derived from the intraocular pressure value. Based on the retinal blood pressure values, which are determined online or preferably offline, local retinal perfusion pressure values (rPP) can be computed and represented in an image of the retina as a pressure mapping image.

13 Claims, 7 Drawing Sheets

(51) Int. Cl.
*A61B 3/18* (2006.01)
*A61B 3/12* (2006.01)
*A61B 5/022* (2006.01)
*A61B 5/00* (2006.01)
*A61B 8/08* (2006.01)
*G06T 7/00* (2017.01)
*A61B 3/14* (2006.01)

(52) U.S. Cl.
CPC ............ *A61B 3/1241* (2013.01); *A61B 5/022* (2013.01); *A61B 5/02216* (2013.01); *A61B 5/6821* (2013.01); *A61B 8/5223* (2013.01); *G06T 7/0012* (2013.01); *G06T 2207/30041* (2013.01)

(56) References Cited

U.S. PATENT DOCUMENTS

| | | | | |
|---|---|---|---|---|
| 6,621,917 | B1* | 9/2003 | Vilser | A61B 3/1233 128/922 |
| 2004/0230124 | A1 | 11/2004 | Querfurth | |
| 2006/0206037 | A1 | 9/2006 | Braxton | |
| 2007/0179382 | A1* | 8/2007 | Vilser | A61B 5/12 600/477 |
| 2010/0056935 | A1* | 3/2010 | McKinley | A61B 5/4041 600/504 |
| 2011/0087086 | A1* | 4/2011 | Falck, Jr | A61B 3/16 600/399 |
| 2014/0358011 | A1* | 12/2014 | Jiang | G06T 7/0012 600/476 |
| 2015/0265172 | A1 | 9/2015 | Fuller et al. | |
| 2017/0065193 | A1* | 3/2017 | Yu | A61B 3/1233 |
| 2020/0170505 | A1* | 6/2020 | Meyer-Schwickerath | A61B 5/02007 |

FOREIGN PATENT DOCUMENTS

| | | |
|---|---|---|
| DE | 19514796 C1 | 9/1996 |
| DE | 102004062337 B4 | 9/2010 |
| EP | 2567656 B1 | 12/2016 |
| WO | 2006091811 A2 | 8/2006 |
| WO | 2015131236 A1 | 9/2015 |
| WO | 2017035406 A2 | 3/2017 |
| WO | 2018121886 A2 | 7/2018 |

OTHER PUBLICATIONS

Measure. (2021). Retrieved Jul. 19, 2021, from www.merriam-webster.com (Year: 2021).*

S. Mojtaba Golzan et al., Dynamic Association between Intraocular Pressure and Spontaneous Pulsations of Retinal Zeins, Current Eye Research, 2011, pp. 53-59, v. 36, No. 1, Informa Healthcare USA, Inc.

William H. Morgan et al., Retinal venous pulsation: Expanding our understanding and use of this enigmatic phenomenon, Progress in Retinal and Eye Research, 2016, pp. 82-107, v. 55, Elsevier.

* cited by examiner

DEVICE AND METHOD FOR DETERMINING RETINAL BLOOD PRESSURE VALUES AND FOR MAPPING RETINAL BLOOD PRESSURE VALUES AND PERFUSION PRESSURE VALUES

RELATED APPLICATIONS

This application claims priority to German Patent Application No. DE 10 2018 107 622.3, filed Mar. 29, 2018, which is incorporated herein by reference in its entirety.

FIELD OF THE INVENTION

The invention relates to a device and a method, using which the intraocular pressure IOP in a patient's eye is increased by artificially applying a variable stimulation pressure SD, thus causing characteristic measurement criteria to appear in the retina of the eye, which allow global and local retinal blood pressure values rP to be derived from the intraocular pressure value IOP. A method and a device of the generic type described herein are known from the DE 195 14 796 C1.

The invention also relates to a device and a method for mapping retinal blood pressure values rP and perfusion pressure values rPP in the optic nerve head (global retinal blood pressure values rP) and in different locations on the retina (local retinal blood pressure values rP) in one or more images of the retina.

BACKGROUND OF THE INVENTION

It is known in modern medicine that changes in the retinal perfusion pressure rPP have a substantial influence on the retinal blood flow and play a decisive role in the genesis of various ocular conditions. The retinal perfusion pressure rPP is calculated from the difference of the retinal arterial blood pressure rPa of the blood flowing into the eye and the retinal venous blood pressure rPv of the blood flowing out of the eye.

$$rPP = rP_a - rP_v$$

In this context, the retinal venous blood pressure rPv depends largely on external circumstances and either assumes the value of the intraocular pressure IOP, if the intraocular pressure IOP is greater than the retinal venous blood pressure outside the eyeball RVP (frequently also referred to as retinal venous outflow pressure), or is equal to the retinal venous blood pressure outside the eyeball RVP, insofar as the latter is greater than the intraocular pressure IOP. In special cases, the retinal venous blood pressure rPV may also assume the value of the intracranial pressure. However, this applies only if the intracranial pressure is greater than the intraocular pressure IOP and the retinal venous blood pressure outside the eyeball RVP.

Ophthalmodynamometry is a method for determining global retinal blood pressure values rP on the basis of known visual pulsation phenomena visible upon reaching the retinal blood pressure values rP. For retinal blood pressure measurement (ophthalmodynamometry), the intraocular pressure IOP is increased. Similar to blood pressure measurement on the upper arm, the intraocular pressure IOP is first increased, at the start of measurement, to suprasystolic arterial blood pressure values greater than the retinal arterial systolic blood pressure value $rP_{asys}$, which are achieved as soon as no vascular pulsation is visible, and then the intraocular pressure IOP is slowly decreased. The first visible arterial vascular pulsations are the visual measurement criterion for reaching the global retinal arterial systolic blood pressure $rP_{asys}$ in the retina. Seeing the arterial vascular pulsations disappear again (further visual measurement criterion) means that the intraocular pressure IOP has reached the retinal arterial diastolic blood pressure $rP_{adia}$ in the retina. In recent years, ophthalmodynamometry has been used increasingly to measure the retinal venous blood pressure inside the eyeball rPv. The visual measurement criterion used for this purpose is the so-called venous collapse in the area of the optic nerve head. The venous collapse occurs in the area of the optic nerve head at the point where the retinal veins exit from the eyeball, provided the intraocular pressure IOP is greater than the retinal venous blood pressure outside the eyeball RVP. If the retinal venous blood pressure outside the eyeball RVP is greater than the intraocular pressure IOP, no spontaneous venous collapse occurs. In order to measure the retinal venous blood pressure outside the eyeball RVP, the intraocular pressure IOP is increased until the spontaneous venous collapse is just visible. The associated intraocular pressure IOP then corresponds to the retinal venous blood pressure outside the eyeball RVP.

A known device used in medicine to perform ophthalmodynamometry is described in the aforementioned DE 195 14 796 C1. In this case, an examiner places a contact lens on the cornea of the eye. Via the contact lens, the examiner observes the optic nerve head of the eye, while increasing the pressure on the eye via the contact lens, thereby increasing the intraocular pressure IOP in the eye, until the visual measurement criteria are visible. The force of the pressure which the contact lens applies to the eye is measured and displayed by a contact lens dynamometer. The intraocular pressure value IOP or retinal blood pressure value rP associated with the respective visual measurement criterion can then be calculated on the basis of said force.

In order to be able to precisely derive the intraocular pressure IOP from the measured pressure at which the examiner presses the contact lens dynamometer onto the patient's eye, calibration of the device is required and has to be repeated periodically. For calibration, a "standard eye" is assumed, i.e. the occurrence of different eye shapes as well as different ocular tissue parameters is not taken into consideration. The manual application of force or pressure to the eye also presents considerable potential for error.

A further device used to perform ophthalmodynamometry is described in DE 35 11 938 A1. In this case, the artificial increase in the intraocular pressure IOP is achieved with the help of suction cup compression tonometry by temporally fixing a suction cup manually on the patient's eyeball by vacuum pressure and then increasing the vacuum pressure within the suction cup. This increase in vacuum pressure within the suction cup causes the patient's eyeball to be sucked increasingly strongly into the suction cup. The resulting deformation of the eyeball leads to an increase in the intraocular pressure IOP. Via the direct contact with the patient's eye, the ocular pulsations are registered and recorded with the help of a conversion unit which is pneumatically connected with the suction cup. By evaluating the curves thus recorded and the calibrated correlation between the vacuum pressure within the suction cup and the intraocular pressure IOP, the different retinal blood pressure values rP can be determined. These include the retinal arterial systolic blood pressure $rP_{asys}$, the ciliary arterial systolic blood pressure and the ocular arterial diastolic blood pressure. Moreover, a number of further parameters relating to the eye, such as ocular perfusion, autoregulatory capacity and the critical point at which the ocular pulse blood volume drops, can also be determined.

The device disclosed in the aforementioned DE 35 11 938 A1 also has to be calibrated regularly due to the increase in intraocular pressure IOP being determined directly on the basis of the vacuum pressure within the suction cup. Moreover, this methodology allows the retinal venous blood pressure outside the eyeball RVP to be measured only to a limited extent, because the intraocular pressure IOP is already increased by the vacuum pressure applied to fix the suction cup. Since the retinal venous blood pressure outside the eyeball RVP is often in the range of the intraocular pressure IOP or slightly higher, this increase in the intraocular pressure IOP required to fix the suction cup may already substantially exceed the starting point of the spontaneous venous collapse and may thus make it impossible to measure the retinal venous blood pressure outside the eyeball RVP. Moreover, no observation of the retina takes place during the examination, thereby allowing evaluation only via the ocular pulsation curves, so that it is questionable whether the retinal blood pressures rP that can be measured by the suction cup method are identical with the global retinal blood pressure values rP initially defined.

Both above-described devices were not originally intended for measuring the retinal venous blood pressure outside the eyeball RVP, but serve to measure global retinal arterial blood pressures rPa, which can be used in some cases to compute further ocular parameters.

Another application consists in measuring intracranial pressure. However, this is only possible if the intracranial pressure is greater than the intraocular pressure IOP and the retinal venous blood pressure outside the eyeball RVP. In this case, the retinal venous blood pressure rPv or the retinal venous blood pressure outside the eyeball RVP, respectively, assumes the value of the intracranial pressure. The intracranial pressure may be determined, in this case, by measuring the retinal venous blood pressure outside the eyeball RVP. Again, the spontaneous venous collapse or other derivable measurement criteria are used as examination criteria, depending on the measurement method and derived measurement criterion used. Devices using this methodology are described, for example, in EP 2 567 656 B1, US 2015/0265172 A1 and DE 10 55 175 B.

Basically, it can be said, however, that all devices described herein are suitable only to determine global retinal blood pressure values rP and, thus, it is only possible to determine a global retinal perfusion pressure value rPP, and that substantial sources of error, in particular by manual application of force or pressure via the calibration correlations, falsify the examination result.

In many cases, it may be clinically useful or required not only to know the global retinal blood pressures rP, but also to measure local retinal blood pressures rP and to evaluate them with respect to their location on the retina, as in the case of arterial and venous vessel occlusions, for example. Moreover, it may be required to examine local retinal perfusion pressures rPP of individual capillary regions and larger vascular regions (vascular networks) and to evaluate and recognize them with a view to predictions or early detection of endangered perfusion pressure ratios and ranges.

SUMMARY OF THE INVENTION

It is the object of the invention to provide a device and a method by which global and local retinal blood pressure values rP can be determined manually, but advantageously also automatically. The retinal blood pressure values rP are to be assignable to a measurement location or to a measurement range comprising a plurality of measurement locations on the retina or the optic nerve head, respectively. Advantageously, perfusion pressure values rPP are to be determined and represented on the basis of the retinal blood pressure values rP.

Another object of the invention is to considerably increase the individual reproducibility of the measurement results, largely eliminate the influence of individual features of the eyeball and significantly reduce the sources of error of manual pressure application and, above all, to make the measurement results independent of the features of the individual eye.

The essence of the invention consists, on the one hand, in that—in addition to the known visual measurement criteria, described above, for determining the global retinal blood pressure values rP—further subjective, but also objective, local pulsation phenomena, signals and measurement criteria of the vascular system of the retina and of the optic nerve head are used or generated or derived, respectively, to which locally and physiologically definable retinal blood pressure values rP can be assigned according to the invention. Advantageously, the blood pressure values rP and/or perfusion pressure values rPP are represented in a locally assigned manner in a pressure mapping image or in a locally and temporally assigned manner in a sequence of pressure mapping images whose background is an image of the retina. According to the invention, the examinations may continue to be performed manually, but may also be performed as automatic measurements.

On the other hand, the device and method are configured such, according to the invention, that the measured retinal blood pressures rP are not determined via unreliable global calibrated correlations between the variable stimulation pressure SD and the intraocular pressure IOP, but are measured directly by the tonometer on the individual patient's eye or are calculated on the basis of an individual relationship of a correlation, directly determined at the patient's eye, between the variable stimulation pressure SD and the intraocular pressure IOP. The central element, in this case, is a unit for generating and applying a variable stimulation pressure, whose pressure-conveying unit, a pressure applicator, is fixed to the patient's head and applies a variable stimulation pressure SD laterally (outside the cornea), directed nasally towards the eyeball, with the correlation between the variable stimulation pressure SD and the intraocular pressure IOP not being exactly known or having been determined for this eye directly at the eye. This lateral arrangement of the pressure applicator with respect to the eye keeps the eye free for inspection through various devices, and tonometer measurements on the eye concerned can also be performed using various devices.

Both of the above-described key aspects of the invention are advantageously carried out jointly, but may also be employed individually, according to the invention, as inventive solutions.

In a device for determining global and local retinal blood pressure values rP in a patient's eye, which device includes a unit acting on the eye to generate and apply a variable stimulation pressure and an imaging unit, the object of the invention is achieved in that a tonometer is provided to measure an intraocular pressure IOP in the eye, said intraocular pressure IOP changing as a function of the applied variable stimulation pressure SD, a computing and control unit including an input and output unit is provided and is connected to the unit for generating and applying a variable stimulation pressure, and the unit for generating and applying a variable stimulation pressure comprises a pressure applicator, which can be attached to the patient's head, fixed with respect to the eye, outside the cornea and outside a light path of the imaging unit, in pressure-free, planar contact with the eye.

Advantageously, the unit for generating and applying a variable stimulation pressure is controllable such that the applied variable stimulation pressure SD can be changed in the direction and speed of an increase as well as kept constant, and the input and output unit is configured to be controlled by an examiner via the input and output unit.

The imaging unit advantageously comprises a digital image sensor or an imaging unit based on optical coherence tomography or on laser-scanning technology and a digital video recorder which is connected to the imaging unit and to the computing and control unit, and the input and output unit comprises a monitor and is configured such that the examiner can either watch online images from the imaging unit or video sequences of the images recorded by the digital video recorder and use them for examination.

Preferably, a data and image evaluation unit is present, in communication with the digital video recorder, the imaging unit, the computing and control unit and the input and output unit, and the input and output unit is configured such that the examiner can define measurement locations for detected visual measurement criteria, in images from the imaging unit or images of the video sequences of the digital video recorder which are displayed on the monitor, and can store the coordinates of the measurement locations together with the visual measurement criteria, each assigned to a respective retinal blood pressure reading rP, and enter them into a pressure mapping image.

The unit for generating and applying a variable stimulation pressure advantageously includes a pressure sensor, allowing a variable stimulation pressure value SD to be assigned to each measured intraocular pressure value IOP or to each image of the video sequence, respectively.

It is further advantageous if the imaging unit comprises a digital image sensor or an imaging unit based on optical coherence tomography or on laser-scanning technology for generating a video sequence, and a data and image evaluation unit as well as a signal analysis unit are present, the data and image evaluation unit being configured to generate a movement-corrected video sequence of the retina of the eye, and forming a signal for each pixel or for any pixel geometry of images of the video sequence and assigning said signal to a time signal of the computing and control unit.

Moreover, it is advantageous if the imaging unit is a modified retinal camera with at least two color channels and a dual band-pass filter and if a unit for generating spectral quotient signals is present, which generates, for each pixel or an aggregate pixel geometry of the images of the video sequence, an illumination-independent spectral quotient signal and assigns said signal to a time signal of the computing and control unit.

Preferably, a unit for generating vessel diameter signals is present, which generates, for each vascular segment, a vessel diameter signal correlating with a diameter and assigns said signal to a time signal of the computing and control unit.

Further, the tonometer is preferably an automatically measuring rebound tonometer or non-contact tonometer and is integrated in the imaging unit.

The object of the invention is further achieved by a method for determining global and local retinal blood pressure values in a patient's eye, wherein a variable stimulation pressure SD is applied to the eye, leading to a change in the intraocular pressure IOP in the eye. At the same time, the retina is being watched and/or a video sequence of images of the retina is recorded. In this case, a current intraocular pressure value IOP is equated to one of the retinal blood pressure values rP if compliance with a characteristic measurement criterion for said retinal blood pressure value rP is observed on the retina or derived from the images. In at least one point in time of compliance, the variable stimulation pressure SD is kept constant over a period of time. During said period of time, a direct measurement of the intraocular pressure IOP is performed manually or automatically using a tonometer, and the measured intraocular pressure value IOP is directly equated to that one of the retinal blood pressure values rP for which the characteristic criterion was met. It is further advantageous, if a time signal is generated to which the measured intraocular pressure values IOP, stimulation pressure values SD, images and derived images of the video sequence as well as points in time of occurrence of the characteristic measurement criteria and the associated retinal blood pressure values rP are assigned.

Preferably, at least two directly measured intraocular pressure values IOP and the stimulation pressure values SD respectively assigned via the time signal are used to compute the individual correlation, applying to the individual eye, between the intraocular pressure IOP and the variable stimulation pressure SD, wherein in the case of only one intraocular pressure value IOP measured directly upon detection of one of the characteristic measurement criteria, another intraocular pressure value IOP is measured directly at any point in time during elevated stimulation pressure values SD, without detection of any of the characteristic measurement criteria.

Preferably, an examiner derives the occurrence of the characteristic measurement criteria of global retinal blood pressure values rP online from the images during the recording of the video sequence. Later, the examiner interactively marks, locally and temporally, the presence of the characteristic measurement criteria of local retinal blood pressures rP offline in measurement locations in the images, determines the respective intraocular pressure values IOP in each case via the time signal, equates each of them to a respective retinal blood pressure value rP, stores the retinal blood pressure values rP and the respective measurement locations and enters them in a pressure mapping image.

In this context, it is advantageous if further vessel diameter signals are derived from the video sequence and are each assigned to a respective point in time and to a vascular segment or to a vascular section comprising vascular segments.

Further advantageously, illumination-independent, spectrally normalized signals are derived from the images of the video sequence and assigned to a point in time and a measurement location.

The signals preferably have assigned to them the rise and fall of vascular pulsations or pulsatory and continuous pallor or signal changes as further characteristic measurement criteria and/or global or local retinal blood pressures rP as further threshold values, and the further characteristic measurement criteria and/or further threshold values are used for automatic measurement or determination of the intraocular pressure values IOP.

The characteristic measurement criteria are preferably detected over the entire retina, deriving therefrom retinal regions which represent pathological vascular regions that can be considered specifically when analyzing the vascular risk of local retinal circulation problems.

In this case, it is advantageous if the measurement locations or vascular segments in which the same measurement criteria occur at the same time are combined to vascular sections or vascular regions and assembled in a pressure mapping image and if different retinal blood pressure values rP and/or measurement criteria are presented in a color-coded manner.

Further advantageously, local retinal perfusion pressure values rPP are obtained from local retinal arterial blood pressure values rPa by approximative calculation as differences between the local retinal arterial blood pressure values rPa and a resting intraocular pressure value $IOP_0$ or a retinal, venous blood pressure value outside the eyeball RVP (for $RVP>IOP_0$) and are represented in the pressure mapping image.

BRIEF DESCRIPTION OF THE DRAWINGS

The invention will be explained in more detail below by way of exemplary embodiments and with reference to drawings, wherein.

DETAILED DESCRIPTION OF THE PREFERRED EMBODIMENTS

The first exemplary embodiment describes a simple design of a method according to the invention and a suitable device, either of which allows the global retinal blood pressure values rP to be determined manually, by visual measurement criteria, without the above-described prior art sources of error. As already explained at the beginning, the global retinal blood pressure values rP can then be used to compute the global retinal perfusion pressure value rPP.

Figure 1:
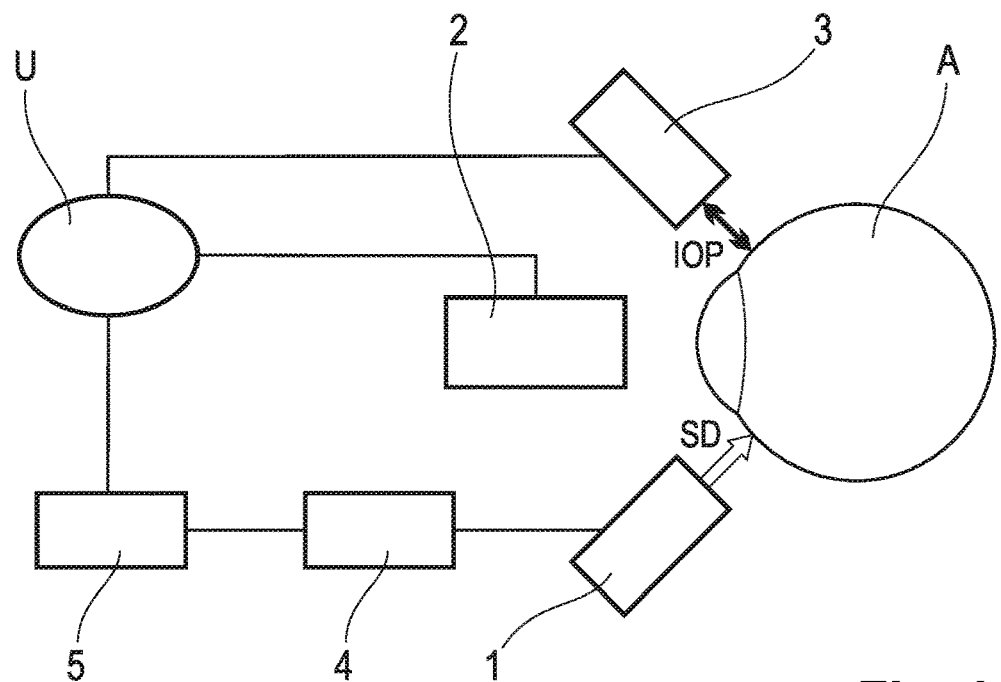
FIG. 1 shows a block diagram for a first exemplary embodiment of a device according to the invention.
Figure 4:
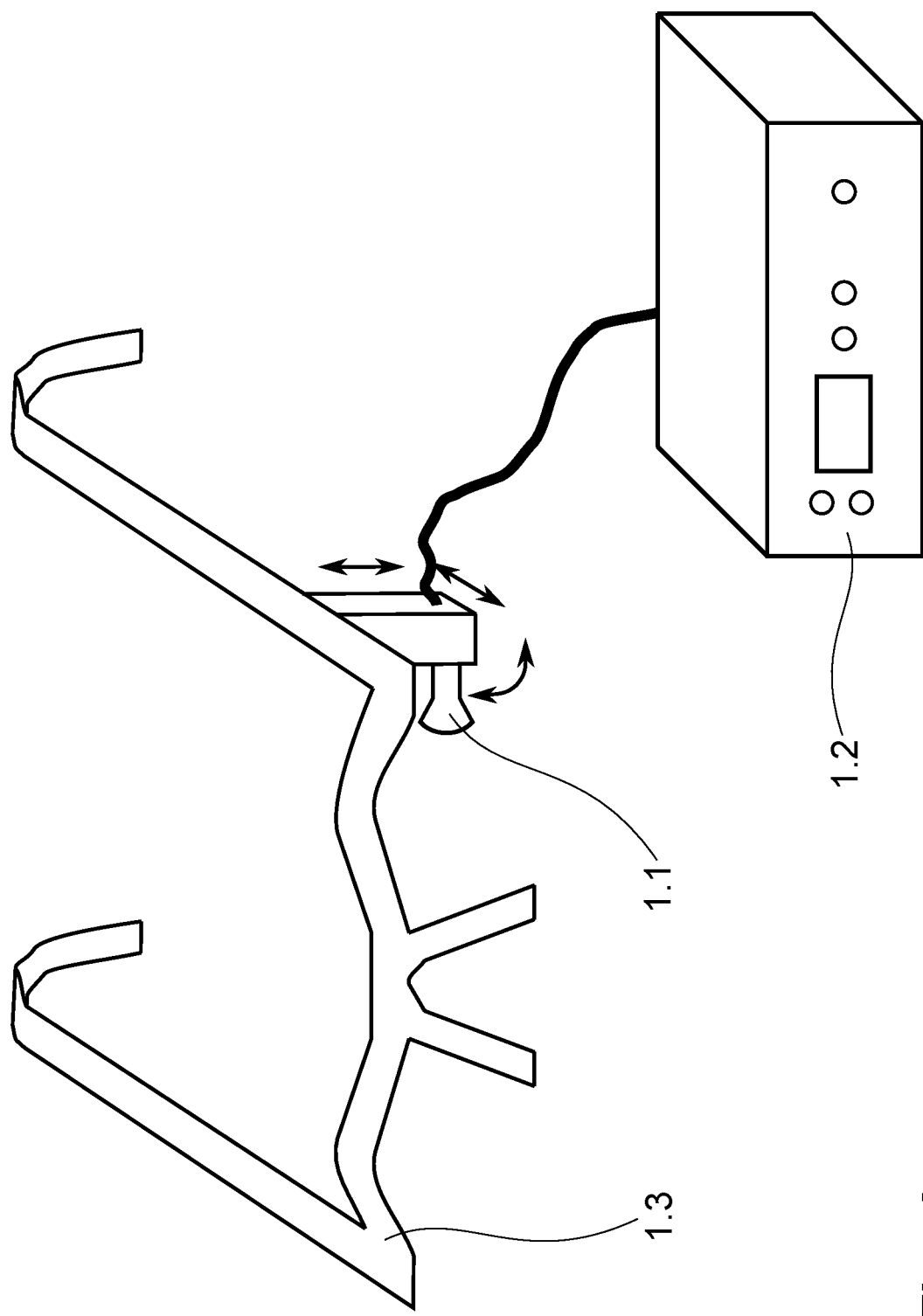
FIG. 4 shows a schematic diagram of a unit for generating and applying a variable stimulation pressure.

All embodiments of a device according to the invention include, similar to this first exemplary embodiment as shown in a block diagram in FIG. 1, at least one unit for generating and applying a variable stimulation pressure 1, a computing and control unit 4, an imaging unit 2 and a tonometer 3. The unit for generating and applying a variable stimulation pressure 1, schematically shown in FIG. 4, comprises a pressure generating unit 1.2, a holder 1.3 and a pressure applicator 1.1, which is fixed to the patient's right or left eye A laterally (temporally), in each case, via the holder 1.3, which preferably resembles a pair of glasses. The pressure applicator 1.1 can be placed in pressure-free, planar contact with the patient's eye A to be examined.

The pressure applicator 1.1 serves to apply a variable stimulation pressure SD onto the patient's eye A to be examined and, according to the first exemplary embodiment, is a small pneumatic balloon, but might also be, for example, a die, a suction cup or an hydraulic system.

In contrast to the already known methods, the embodiment of the pressure applicator 1.1 as a small pneumatic balloon has a number of advantages. For instance, there is a much lower risk of injury from sharp rims, which are produced on the edges of pressure applicators 1.1 made of metals, plastic materials or ceramics or other solid materials. Moreover, the soft surface of the balloon is much more pleasant for the patient during the examination. In addition, the uniform expansion of the balloon in all directions avoids transverse forces which may result in falsified measurement results.

Connected to the pressure applicator 1.1 is the pressure generating unit 1.2, by which the variable stimulation pressure SD can be generated, increased, decreased or kept constant.

In order to generate the variable stimulation pressure SD in a controlled manner, the unit for generating and applying a variable stimulation pressure 1 is connected to the computing and control unit 4. Depending on the pressure applicator 1.1 selected, the unit for generating and applying a variable stimulation pressure 1 may comprise, as the pressure generating unit 1.2, for example, a pump, a system consisting of a pneumatic cylinder and a piston or/and control electronics for linear drives. In this first exemplary embodiment, the pressure generating unit 1.2 is a pneumatic system consisting of a pneumatic cylinder and a piston which can be moved in the pneumatic cylinder by a linear drive. By moving the piston, the air contained in the pneumatic system is compressed or dilated, causing the pressure in the pressure applicator 1.1 either to increase or to decrease. The pressure generating unit 1.2 may advantageously comprise components for defined adjustment of the increase or decrease in variable stimulation pressure SD. Possible designs for this include, for example, systems consisting of various throttle valves and magnetic valves, or suitable control electronics which allow different speeds of adjustment of a linear drive.

The pressure generating unit 1.2 advantageously comprises components for measuring the variable stimulation pressure SD. Depending on the design of the unit, pressure sensors, force sensors or distance sensors may be used, for example.

The pressure generating unit 1.2 advantageously also comprises a component enabling a sudden drop in the variable stimulation pressure SD. For this purpose, one or more magnetic valves may be used, for example, by which the system is suddenly vented in an emergency.

The holder 1.3 serves to couple the pressure applicator 1.1 directly to the patient's head and may be, for example, a pair of glasses, a head band or a bracket placed on the patient's head. Preferably, the holder 1.3 is implemented in the form of a pair of glasses. In order to improve the coupling of the pressure applicator 1.1 to the patient's head, the holder 1.3 is advantageously provided with a further component, such as a glasses lace, a rubber band or a mechanically adjustable fixing means.

In order to achieve individually adaptable positioning of the pressure applicator 1.1, in particular adjustability of the direction from which the pressure applicator 1.1 is adducted to the patient's eye A, the pressure applicator 1.1 is attached to the holder 1.3 on the patient's eye A in an individually adjustable manner, preferably via height adjustment, distance adjustment and angle adjustment.

The optical access to the retina for the imaging unit 2, and also the light path of the imaging unit 2, must not be impeded and/or blocked by any of the components contained in the unit for generating and applying a variable stimulation pressure 1.

The imaging unit 2 used in the present example is a slit lamp with a Hruby lens through which the examiner U adjusts and observes the optic nerve head at the retina. Instead of the slit lamp, the examiner U may use any device enabling him to examine the optic nerve head at the retina, e.g. an ophthalmoscope, a retinal camera or an OCT.

The tonometer 3 is embodied as an applanation tonometer and mounted to the slit lamp in a known manner. The applanation tonometer is easy to replace manually with the Hruby lens to allow the intraocular pressure IOP to be measured according to the method of the invention (tonometer measurements).

The computing and control unit 4 is connected to the unit for generating and applying a variable stimulation pressure 1 and a simple input and output unit 5 by signaling technology, allowing the examiner U to control the unit for generating and applying a variable stimulation pressure 1 via the input and output unit 5 and the computing and control unit 4. The input and output unit 5 is equipped with a double footswitch for signaling by the examiner U, who increases the variable stimulation pressure SD by actuating the right pedal button and decreases the variable stimulation pressure SD by actuating the left pedal button. The increase or decrease in variable stimulation pressure SD is more rapid, the harder the pedal buttons are pressed. Releasing the pedal button triggers a stop signal for the change in variable stimulation pressure SD from the input and output unit 5 and the computing and control unit 4 to the unit for generating and applying a variable stimulation pressure 1.

A device according to the first exemplary embodiment is provided, in particular, for determining global retinal blood pressure values rP from which, as already explained at the beginning, the global retinal perfusion pressure rPP can be computed. However, the device may also be put to multiple use for determining local retinal blood pressure values rP in a plurality of locally different peripheral retinal regions.

The method will be described below in individual process steps using a device according to the first exemplary embodiment.

Step 1-0:
The examiner U ascertains that no spontaneous venous collapse is visible on the optic nerve head. If this is the case, the retinal venous blood pressure value outside the eyeball RVP must be used, instead of the resting intraocular pressure value $IOP_0$, to compute the retinal perfusion pressure value rPP. Prior to the examination, the examiner U makes sure that the pressure applicator 1.1 has been fully vented and is in direct contact with the eye A.

Step 1-1:
Before the examination, the examiner U first measures the resting intraocular pressure $IOP_0$, using an applanation tonometer as the tonometer 3, and enters the pressure value into the computing and control unit 4 so as to store it or logs said value.

Step 1-2:
The examiner U replaces the applanation tonometer with the Hruby lens, adjusts the optic nerve head using the slit lamp and, pressing the right pedal button, begins to increase the variable stimulation pressure SD via the input and output unit 5 and the computing and control unit 4 while observing the veins of the optic nerve head. The computing and control unit 4 controls the rate at which the stimulation pressure increases as a function of how strongly the right pedal button is actuated and, simultaneously with the first actuation, triggers the start signal. Beginning with the start signal, the computing and control unit 4 adopts the stimulation pressure values SD from the unit for generating and applying a variable stimulation pressure 1 and records them as a function of time. For better detection of pulsation phenomena, the examiner U can increase and decrease the variable stimulation pressures SD as fast and as long as desired by changing between the right and left pedal buttons.

Step 1-3:
Upon the first visible appearance of the spontaneous venous collapse, the examiner U triggers the stop signal via the input and output unit 5 and the computing and control unit 4 by taking his feet off the pedal button, thereby stopping any further increase or decrease in variable stimulation pressure SD in the unit for generating and applying a variable stimulation pressure 1 and keeping the variable stimulation pressure SD constant.

Step 1-4:
The examiner U replaces the Hruby lens with the applanation tonometer, measures the current intraocular pressure IOP and logs said value or enters said value via the input and output unit 5 into the computing and control unit 4, where this value is stored as the retinal venous blood pressure outside the eyeball RVP together with the recorded time value at the time of the stop signal.

Step 1-5:
The examiner U continues to observe the optic nerve head and now quickly increases the variable stimulation pressure SD to retinal suprasystolic blood pressure values rP by further actuating the right pedal button. The computing and control unit 4 continues to record the variable stimulation pressure SD as a function of time. Upon reaching retinal suprasystolic blood pressure values rP, i. e. retinal blood pressure values rP above the retinal arterial systolic blood pressure $rP_{asys}$, the examiner U actuates the left foot switch and slowly decreases the variable stimulation pressure SD again.

Step 1-6:
Upon detecting the first arterial pulsations in the area of the optic nerve head, the examiner U takes his foot off the right pedal button, thereby triggering a stop signal, and the variable stimulation pressure SD is kept constant. The examiner U measures the intraocular pressure IOP and logs said pressure or enters said pressure into the computing and control unit 4 via the input and output unit 5. The intraocular pressure value IOP is stored in the computing and control unit 4 as a global retinal arterial systolic blood pressure value $rP_{asys}$ and assigned to the time signal s(t) at the time of the stop signal.

Step 1-7:
The examiner U regards the optic nerve head again and continues to decrease the variable stimulation pressure SD until the strong arterial pulsations on the optic nerve head just disappear. Then, the examiner U takes his foot off the right foot switch, thereby in turn triggering a stop signal, measures the intraocular pressure IOP and enters the obtained intraocular pressure value IOP into the computing and control unit 4 via the input and output unit 5. The computing and control unit 4 stores said intraocular pressure value IOP as a retinal arterial diastolic blood pressure value $rP_{adia}$ and assigns said value to the time dependency.

Step 1-8:
The examiner U ends the examination by quickly decreasing the variable stimulation pressure SD to zero, which also causes the computing and control unit 4 to complete the examination procedure, completely relieving the pressure system and ending the time recording. The time recording of the stimulation pressure and intraocular pressure values SD, IOP is used to generate an individual regression line computing the correlation between the intraocular pressure IOP and the variable stimulation pressure SD for each stimulation pressure value SD. This correlation is stored for further examinations of the person in question and of the eye A in question. Based on the global retinal blood pressure values rP, the computing and control unit 4 now computes the global retinal perfusion pressure value rPP and outputs it in an examination report together with the other retinal blood pressure values rP.

As an alternative, the measurement of the intraocular pressure IOP, which is equated to the retinal arterial systolic blood pressure $rP_{asys}$, can be dispensed with. After the stop signal in step 1-6, instead of measuring the intraocular pressure IOP, the examiner U merely triggers a signal which is stored in the time signal s(t) by the computing and control unit 4. In step 1-8, the value of the retinal arterial systolic blood pressure $rP_{asys}$ is then computed on the basis of the regression line IOP=f(SD). In this manner, the for examination can be reduced because the retinal arterial systolic blood pressure $rP_{asys}$ is not measured, but can be computed by means of the regression line.

In order to make the computation of the correlation between the intraocular pressure IOP and the variable stimulation pressure SD more accurate, stops with IOP measurements may further be inserted during the above-described method.

To avoid errors due to the effect of tonography, the tonometer measurements are completed within 1 min at the most. Using a rebound tonometer, the IOP measurements can be carried out within seconds.

The proposed method according to the invention may also be used analogously to measure only one of the retinal blood pressures rP, such as the retinal venous blood pressure outside the eyeball RVP, for example. In this case, the examination is aborted already after step 1-4, and the measurement of the variable stimulation pressure SD by the unit for generating and applying a variable stimulation pressure 1 can be dispensed with, because no individual relationship between the intraocular pressure IOP and the variable stimulation pressure SD is required.

In a second exemplary embodiment of a device according to the invention and a second exemplary embodiment of a method according to the invention, the examiner U manually determines, in a manner similar to the first exemplary embodiment, global retinal blood pressure values rP online by visual measurement criteria and then additionally determines local retinal blood pressure values rP by offline evaluation of a video sequence recorded during the first examination.

Local retinal perfusion pressure values rPP can also be determined by approximative calculation based on local retinal arterial blood pressure values rPa. Since the venous flow path up to the point where the venous vessels exit from the eyeball usually represents the low pressure area and only very moderate venous flow resistance are to be expected as well, it is assumed by approximation that the local retinal perfusion pressure value rPP can be computed from the local retinal arterial blood pressure value rPA determined by the method, minus the resting intraocular pressure value IOP0 or the retinal venous blood pressure value outside the eyeball RVP (depending on which is the greater value).

Manually determining local retinal blood pressure values rP in turn means observing visual pulse criteria, such as those observed in order to determine the global retinal blood pressure values rP at the optic nerve head, in selected vascular regions in vascular sections and/or selected capillary regions in order to determine the associated retinal blood pressure values rP in the observed locations of the retina and, optionally, compute the associated retinal perfusion pressure values rPP.

Local visual pulse criteria include, above all, the quick increase of strong diameter pulsations up to vascular occlusions, or even capillary, pulse-like pallor up to complete capillary occlusion, which becomes visible as complete pallor. According to the invention, local retinal blood pressures rP defined on the basis of microcirculation, such as the critical arterial or capillary blood pressure (retinal arterial critical blood pressure $rPa_{krit}$) or the retinal arterial or capillary occlusion pressure (retinal arterial occlusion pressure $rPa_{VS}$), for example, are used which occur upon reduction of the retinal perfusion pressure rPP by strong pulsations at a retinal arterial critical blood pressure value $rPa_{krit}$ up to vascular occlusion, which occurs at a retinal arterial occlusion pressure value $rPa_{VS}$ and are determined as special pathophysiological, defined local retinal blood pressures rP.

Determining local retinal blood pressure values rP, in particular the retinal arterial occlusion pressure value $rPa_{VS}$, is of particular clinical advantage in the case of local circulation problems of the retina, e.g. vessel occlusions, or upon failure or restriction of local vascular regions, e.g. in the case of diabetic retinopathy, glaucoma and other conditions. On the other hand, retinal arterial critical blood pressures $rPa_{krit}$ and retinal perfusion pressures rPP have predictive value and may enable early functional detection of critical circulation conditions.

The second exemplary embodiment represents an inventive extension of the first exemplary embodiment both in terms of the device and of the method.

Figure 2:
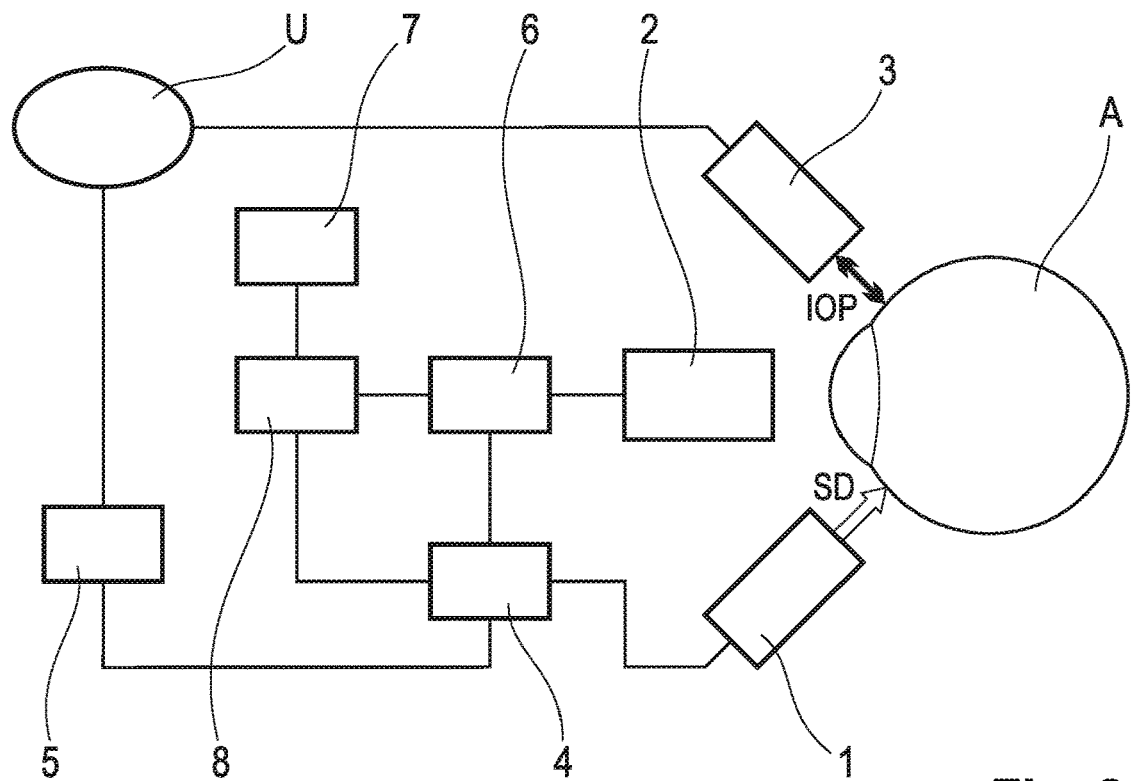
FIG. 2 shows a block diagram for a second exemplary embodiment of a device according to the invention.

The inventive extension of the device is shown in FIG. 2. Instead of the slit lamp according to the first exemplary embodiment, a retinal camera with a digital image-recording unit is now used as the imaging unit 2 and is connected to a digital video recorder 6 to which the recorded video sequence is fed. Moreover, the device includes a results storage unit 7 and a data and image evaluation unit 8 connected thereto, the latter being in turn connected, as is the digital video recorder 6, to the central computing and control unit 4 via signaling pathways. The input and output unit 5 includes a monitor for displaying the video sequences and for presenting the results. Advantageously, the tonometer 3 used is not an applanation tonometer, but a rebound tonometer.

On the input side, the digital video recorder 6 is connected to the computing and control unit 4 via a signaling pathway so as to be controlled synchronously with the unit for generating and applying a variable stimulation pressure 1 in response to a time signal s(t). Via this signal connection to the computing and control unit 4, the control signals, triggered by the examiner U with the help of the input and output unit 5 or input into the computing and control unit, respectively, are also transmitted to the imaging unit 2. Thus, the described signaling pathway serves the purpose of process control of the device. The computing and control unit 4 then temporally assigns to said time signal s(t) all intraocular pressure values IOP or global retinal blood pressure values rP determined, respectively, as well as the local retinal blood pressure values rP obtained later by offline evaluation, with the images and measurement locations in the image assigned to the local retinal blood pressure values rP.

The digital video recorder 6 is connected, via a further signaling pathway, to the data and image evaluation unit 8 where processing and synchronized storage of all data and control signals is effected in response to the time signal s(t). The data and image evaluation unit 8 is also controlled via the computing and control unit 4 to which it is connected via a signaling pathway.

The signaling pathways allow process control of the method described in more detail below via the computing and control unit 4. The control commands input by the examiner U via the input and output unit 5 are transmitted, via a signal line, to the computing and control unit 4, processed there and transmitted to the relevant units.

The input and output unit 5 is used by the examiner U to input data and control commands and to represent and output the respective examination results. During the examination, the stimulation pressure values SD and the video sequence are represented online on the monitor. In this second exemplary embodiment, the examiner U observes the optic nerve head via the monitor, not directly via the slit lamp as in the first exemplary embodiment.

According to the invention, after determining the global retinal blood pressure values rP in accordance with the process steps carried out in the first exemplary embodiment, the offline evaluation of local retinal blood pressure values rP is performed on the basis of the recorded video sequence. Both foot switches (right and left) are then actuated to control the video playback (the speed of the video playback is controlled by the actuation level of the foot switches; the left foot switch rewinds the video sequence and the right foot switch controls the forward playback). Releasing the foot switch stops the playback of the video sequence, and an image of the video sequence is presented as a still image on the monitor. The current stimulation pressure value SD associated with the presented image and/or, optionally, the assigned intraocular pressure value IOP is displayed on the monitor. The basis for this is the computation of the correlation between the variable stimulation pressure SD and the intraocular pressure IOP whose result is obtained already after completion of the determination of the global retinal blood pressure values rP.

The sequence of process steps for offline measurement of local retinal blood pressures rP taken right after the method for determining the global retinal blood pressure values rP is as follows:

Step 2-1:

The examiner U starts the offline evaluation via the input and output unit 5 (process menu item). The results image storage unit 7 and the time signal s(t) are set to s(t)=zero. The digital video recorder 6 starts the first image. A graph in the image shows the first stimulation pressure value SD or the intraocular pressure value IOP, respectively, on the monitor. The input and output unit 5 is switched to interactive mode in the monitor image, and a cursor appears in the image (still image) of the retina in order for the examiner U to mark measurement locations by means of a mouse attached to the input and output unit 5. The foot switches are switched to video control as described above.

Step 2-2:

The examiner U begins to control the video sequence, fast-forwarding or rewinding it with his feet, while observing the vascular regions of interest. Upon occurrence of the pulsation phenomena described above, the examiner U stops the playback.

Step 2-3:

The examiner U uses the mouse to mark the location of the pulsation phenomenon in the still image as a measurement location in the image and then clicks on the retinal blood pressure value rP associated with the pulsation phenomenon in a list. The computing and control unit 4 adopts the retinal blood pressure value rP or the stimulation pressure value SD, respectively, associated with the image, converts the stimulation pressure value SD to the retinal blood pressure value rP, if necessary, and stores the result in the examination report together with an image number of one of the images of the video signal assigned to the time signal s(t) and with the specified measurement location in the image. The examiner U is prompted to specify an associated venous measurement location for computation of the retinal perfusion pressure values rPP in the next step. In the case of retinal arterial critical blood pressure values $rPa_{krit}$, instead of specifying arterial and venous measurement locations, the examiner U may also graphically circumscribe the (pale) capillary region concerned using the mouse.

Upon completion of this step, the examiner U returns to step 2-2, if he wishes to continue to acquire further measurement locations and retinal blood pressures rP, or terminates the process.

Step 2-4:

Upon termination of the process, all retinal blood pressure values rP and their measurement locations are entered into a pressure mapping image, presented to the examiner U and numerically printed in a measurement report.

Figure 6A:
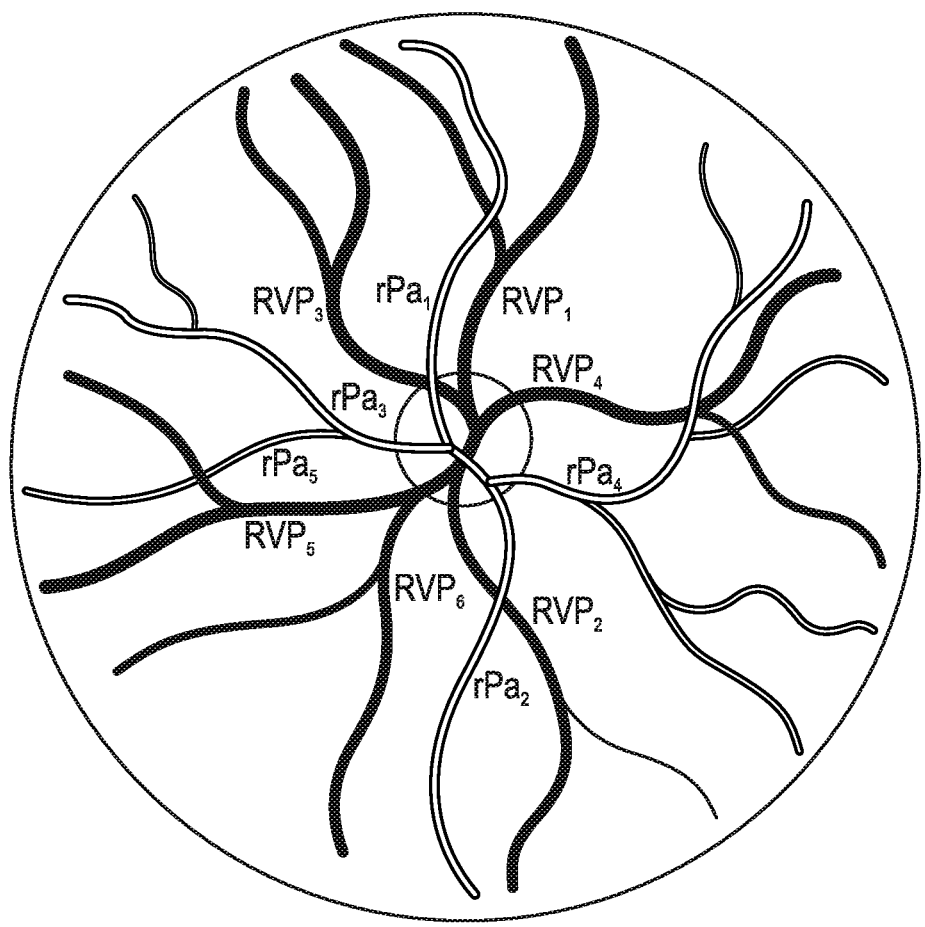
FIGS. 6A, 6B, 6C show examples of pressure mapping images.
Figure 6B:
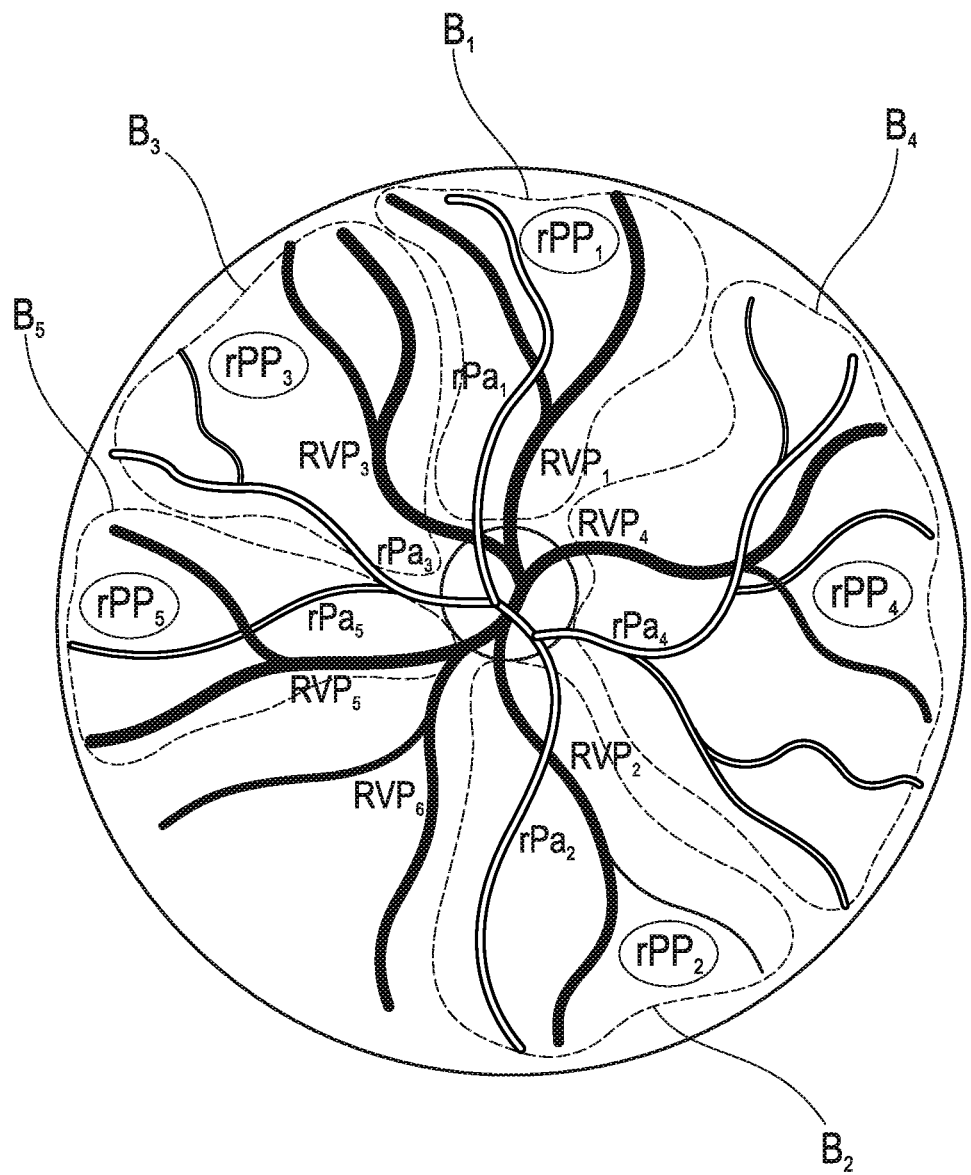
Figure 6C:
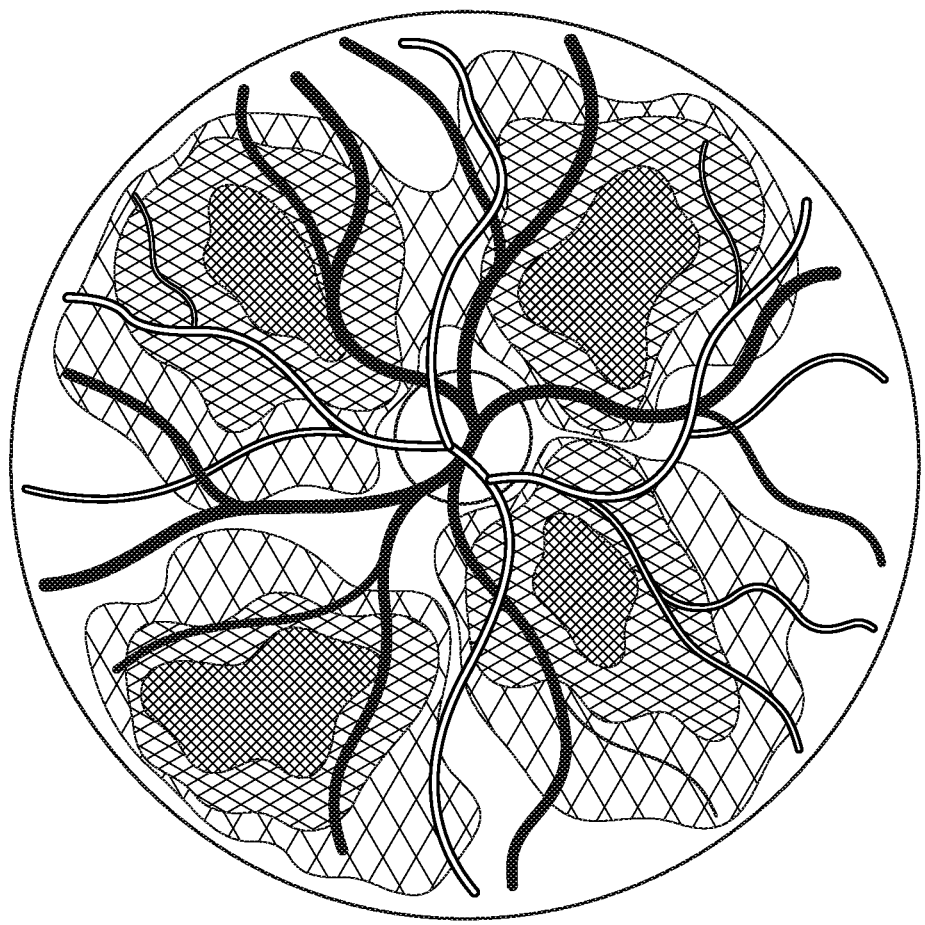

The data and image evaluation unit 8 serves to implement the offline evaluation following the actual examination. It loads the data recorded during the examination and offsets them against one another so that a pressure mapping image, as shown in FIGS. 6a-6c, can be generated by pressure mapping, enabling the visual examination of the local perfusion pressure differences.

In a third exemplary embodiment of a device according to the invention and of a method according to the invention, objective and automatic imaging of the retina (retinal imaging) is performed in addition to determining global and local retinal blood pressure values rP.

Under stationary conditions of blood microcirculation, a network of flow paths with different flow resistances builds up, which concern the capillary regions themselves, but also the vascular sections upstream and downstream of the capillary regions, which respectively form local vascular networks. This results in local distribution of retinal perfusion pressures rPP between the individual local vascular networks and, in particular, individual local capillary regions.

As a result of the local differences in flow resistance, when the intraocular pressure IOP increases or the retinal perfusion pressure rPP decreases or when the retinal arterial blood pressure rPa decreases, respectively, the local vascular networks or the capillary regions, respectively, with high upstream or downstream flow resistances already collapse earlier or can no longer be sufficiently supplied with blood, while other adjacent vascular regions with a lower upstream or downstream flow resistance are still sufficiently supplied with blood.

The collapsing of larger vessels is detectable by strongly increasing pulsations of the vessel diameters and can be used as an objective measurement criterion for retinal arterial occlusion pressures rPaVS. The attainment of retinal arterial critical blood pressure values rPakrit in capillary regions, when local retinal arterial diastolic blood pressure values rPadia are exceeded, is also first characterized by an increase in the pulsations of the regions concerned, followed by occlusion of the capillaries if the intraocular pressure IOP increases further and resulting in the respective capillary region paling and/or turning gray. At the time of complete occlusion of a capillary region, said capillary region reaches its maximum brightness value in the image of the retina. The attainment of a local maximum of brightness may be used as an objective measurement criterion for the attainment of a retinal arterial occlusion pressure rPaVS, and the beginning of the strong capillary pulsations (or of the brightness of the capillary region, respectively) may be used as an objective measurement criterion for a retinal arterial critical blood pressure rPakrit. It is essential for the embodiment according to the invention that, in contrast to the conventional measurement of retinal arterial blood pressures rPa, the intraocular pressure IOP must not drop or be decreased from retinal suprasystolic blood pressure values rP, but must increase or be raised from the resting intraocular pressure value IOP0 before the examination, because otherwise the pressure differences of interest cannot evolve (see process steps).

The method according to the third exemplary embodiment may be advantageously applied to examine the capillary control reserve and as a predictor for capillary failures to be expected in connection with diabetic retinopathy, glaucoma and other conditions.

Figure 3:
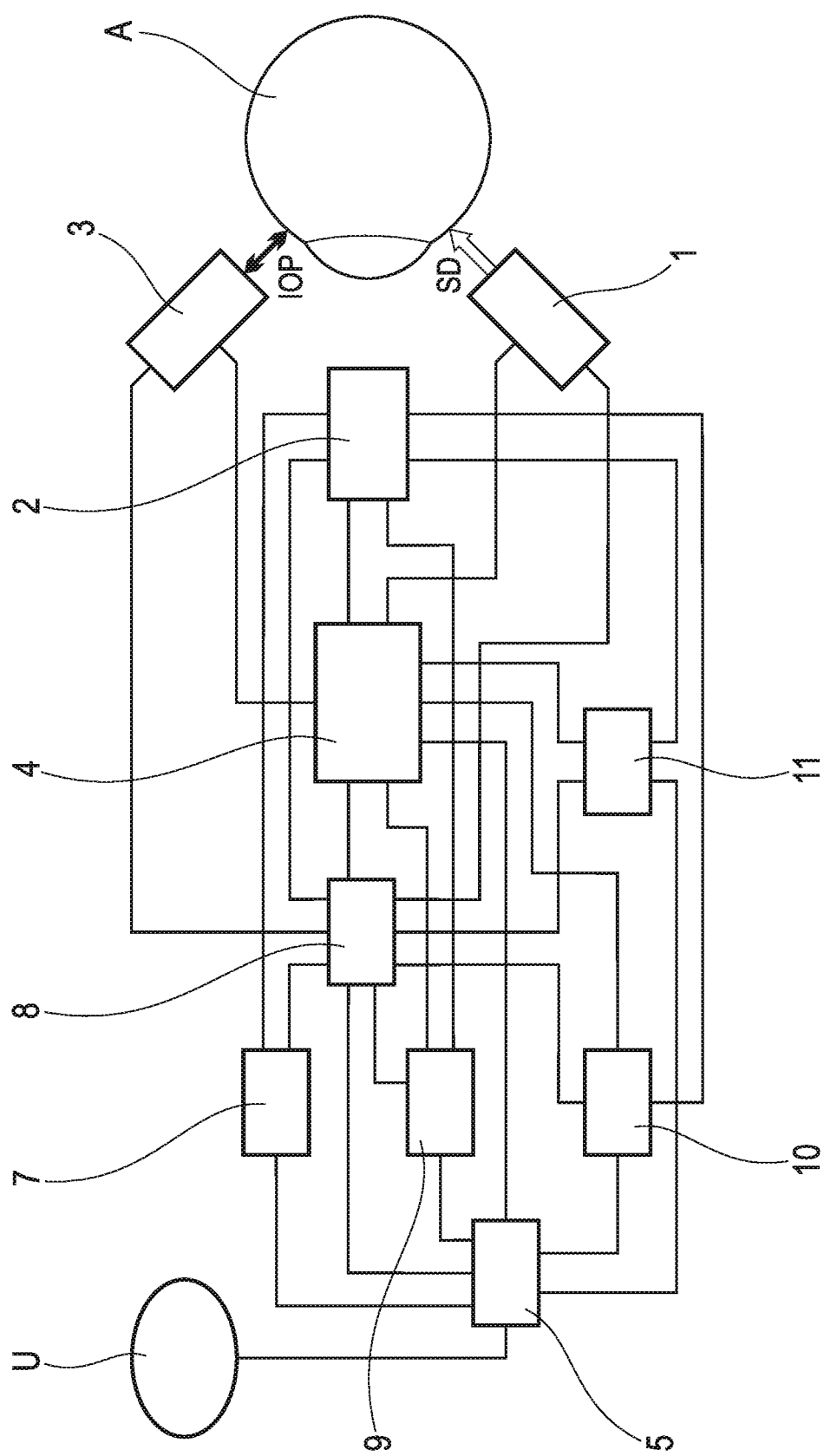
FIG. 3 shows a block diagram for a third exemplary embodiment of a device according to the invention.

As shown in a block diagram in FIG. 3, the third exemplary embodiment also builds on the preceding examples and extends them. The device of the second exemplary embodiment is extended by a signal analysis unit 9, a unit for generating spectral quotient signals 10 and a unit for generating vessel diameter signals 11. In this case, the imaging unit 2 is a spectrally modified retinal camera, and the digital video recorder 6 is omitted. All units 9, 10, 11 are connected to the input and output unit 5 and the data and image evaluation unit 8 as well as to the imaging unit 2. The video sequence is preferably presented to the examiner U together with measurement results and the retinal blood pressure values rP for adjustment of the retina and for tracking and monitoring the adjustment during the examination procedure.

The unit for generating spectral quotient signals 10 serves to eliminate the influence of the illumination intensity on the signals generated for the examination. The spectrally modified retinal camera constitutes the imaging unit 2. According to the invention it comprises, in its illumination beam path an at least dual-band pass filter, e.g. with one spectral range in the red light range and one spectral range in the green light range, respectively adjusted to the spectral sensitivity of a red and a green color channel of the digital image sensor. The adjustment is effected such that neither the red nor the green color channel is responsive to the respective other spectral range of the bandpass filter. The color channels and the bandpass filter are components of the spectrally modified retinal camera. The unit for generating spectral quotient signals 10 is supplied with the video signals from the retinal camera and, pixel by pixel, generates quotients from the intensities of the red color channel, divided by the green color channel, with the pixels having to correspond to the same retina location in the retinal image. This results in a spectrally normalized quotient image, wherein illumination-side differences are eliminated by spectral normalization. The red backscattered light, which substantially penetrates blood, serves as the reference wavelength in this case, with light in the green light range being strongly absorbed by blood and reflecting the blood volume in a retinal region. The quotient describes, regardless of illumination, the blood volume in a capillary region. The resulting quotient image sequence of the retina is stored in the unit for generating spectral quotient signals 10 and then transmitted to the signal analysis unit 9 in accordance with the process steps.

The unit for generating vessel diameter signals 11 determines vessel diameters in selected vascular sections, segment by segment along the vascular sections, as well as from image to image in the green color channel of the video sequence or optionally in the quotient image. The time sequence of the vessel diameters of the individual vascular segments is then used to generate vessel diameter signals which are fed to the signal analysis unit 9.

The invention need not necessarily include both a unit for generating spectral quotient signals 10 and a unit for generating vessel diameter signals 11 and need not necessarily generate spectrally normalized quotient images and signals derived from them. The proposals presented in this exemplary embodiment represent advantageous embodiments.

Here, the tonometer 3 is connected to the computing and control unit 4 and to the data and image evaluation unit 8 via signaling pathways. In contrast to the exemplary embodiments already described, the tonometer 3 is no longer operated manually by the examiner U having to input the measured retinal blood pressures rP via the input and output unit 5, but is directly integrated in the device and controlled by the device fully automatically. In order to achieve this, the tonometer 3 is connected to the computing and control unit 4 via a signaling pathway. This connection serves to transmit the intraocular pressure values IOP which, upon reaching previously defined measurement criteria, trigger an automatically performed measurement of the intraocular pressure IOP. The obtained intraocular pressure values IOP are transmitted to the computing and control unit 4 via a signaling pathway and are synchronized there to the time signal s(t) for further processing. The intraocular pressure values IOP synchronized to the time signal s(t) are transmitted to the data and image evaluation unit 8, via a signaling pathway, for storage and further processing.

In this exemplary embodiment, too, the results storage unit 7 serves the purpose of storage or intermediate storage, respectively, of pressure mapping images.

The vessel diameter signals transmitted to the signal analysis unit 9 for analysis are the time and location-dependent vessel diameter of individual vascular segments or the averaged vessel diameter provided by the unit for generating vessel diameter signals 11 for a vascular section formed by several vascular segments, as well as the unnormalized brightness, averaged over a defined area formed by a pixel or a group of pixels, or/and the averaged quotient of the brightness values of different colors.

The following process steps are carried out in order to perform the automatic measurement of the global retinal blood pressures rP and for pressure mapping.

Step 3-0:

The examiner U attaches the pressure applicator 1.1 to the patient's head such that the pressure applicator 1.1 slightly touches the eye A in the temporal canthus, without exerting pressure.

Then the examiner adjusts the modified retinal camera and the integrated tonometer 3 to the eye A such that automatic tonometer measurements are possible in parallel with retinal imaging and the retinal camera provides an evaluable image of the retina, including the optic nerve head, to the monitor of the input and output unit 5.

The video sequence provided by the imaging unit 2 is examined for sufficient image quality by suitable means. If necessary, the examiner U is asked to correct the image quality by adjusting the retinal camera.

Then the examiner U starts the examination procedure.

Step 3-1:

The computing and control unit 4 initiates an automatic intraocular pressure measurement to obtain an initial value or resting intraocular pressure value $IOP_0$, respectively.

Step 3-2-1:

Now, the variable stimulation pressure SD is increased, while images of the retina forming a video sequence of the retina are generated. The data and image evaluation unit 8 analyzes the images of the video sequence and determines image shifts or rotations, respectively, between adjacent images and corrects the image coordinates so as to generate a movement-corrected video sequence in which identical retinal locations overlap. This movement-corrected video sequence will be assumed below.

The papilla (optic nerve head) and the vessels are selected by suitable means, using the color images or the quotient images to separate arterial and venous vessels from one another. The selected arterial and venous vascular network is stored.

Step 3-2-2:

The unit for generating vessel diameter signals 11 accesses the selected vascular network and determines vessel diameters, segment by segment along the vessels as well as image by image, storing each value assigned to the respective location, time and image.

Step 3-2-3:

The unit for generating spectral quotient signals 10 forms spectrally normalized quotient images from the movement-corrected images of the video sequence, as described above.

Furthermore, quotient signals are generated for all pixels of the quotient images which were not recognized as vessels and, therefore, are not part of the selected vascular network, said quotient signals describing the time curve of the quotient signal per pixel at the measurement location on the retina via the time signal s(t) in the images of the video signals.

Step 3-2-4:

Based on the red or green movement-corrected images (color images) of the video sequence, the data and image evaluation unit 8 also forms the time curve of the time and location-dependent green and/or red color intensity signals for all pixels, except the pixels associated with the selected vascular network.

All signals formed are transmitted to the signal analysis unit 9.

Step 3-3:

The signal analysis unit 9 monitors all signals with respect to the objective measurement criteria defined below.

Step 3-3-1:

The signals on the selected optic nerve head are monitored for the occurrence of a spontaneous venous collapse. The following objective measurement criteria are used:

a) Individual venous vascular segments begin to pulsate multiple times stronger than before and/or also stronger than most venous vascular segments on the optic nerve head. The threshold factor for the resulting change in diameter is defined as factor 3, but may also be adjusted differently on the basis of experimental studies.

b) The quotient signals and/or the red color intensity signals and/or the green color intensity signals increase in pulse amplitude multiple times with respect to before and/or with respect to the adjacent pixels. The threshold factor is defined as factor 3, but it may also be adjusted differently on the basis of experimental studies or set to differ between the various signals.

Figure 5:
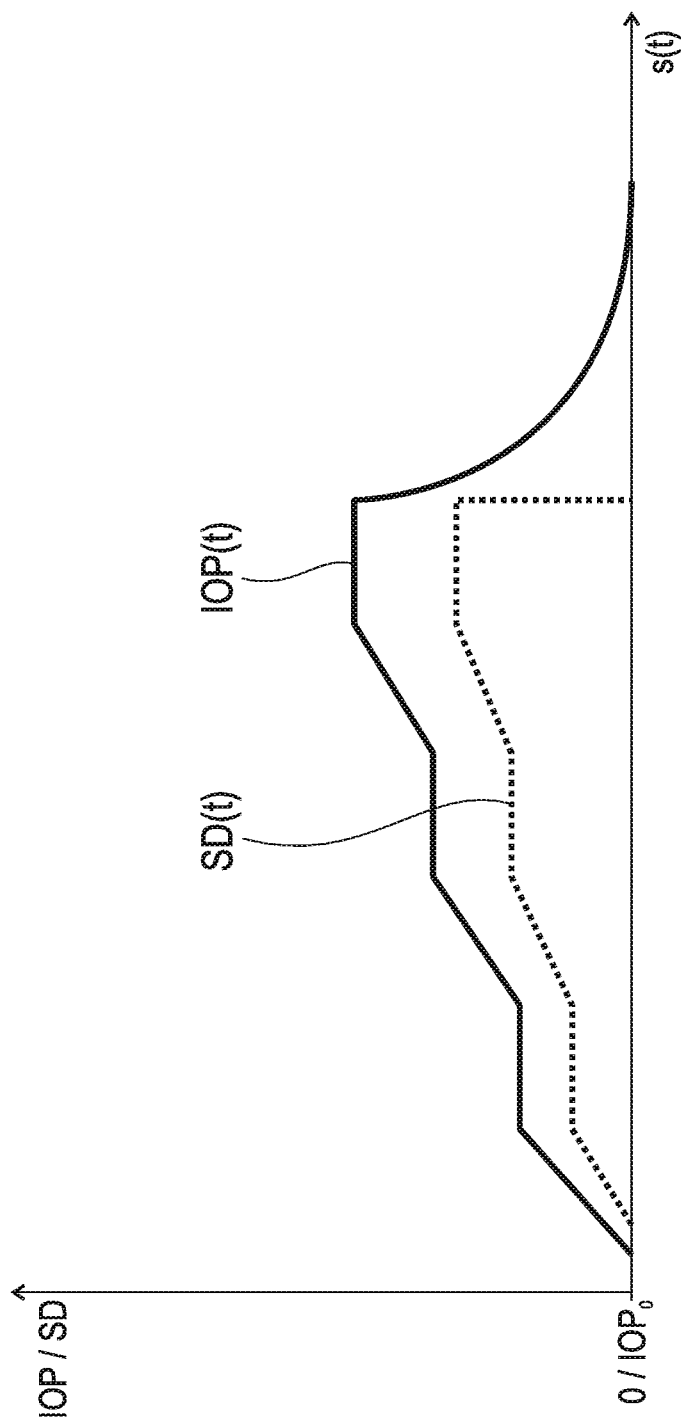
FIG. 5 shows a diagram from which the change in the intraocular pressure IOP as a function of the change in the variable stimulation pressure SD over time is evident.

Step 3-3-2:

The aforementioned signals of the entire retina are monitored for the following local retinal arterial blood pressures rPa:

$rP_{adia}$: retinal arterial diastolic blood pressure:

Criterion: The temporal pulse amplitude of segments of the arterial vessel diameter begins to increase by at least three times the pulse amplitude at lower stimulation pressure values SD $rPa_{krit}$: retinal arterial critical blood pressure Criterion: pulsations of the quotient signals or of the red color intensity signals and the green color intensity signals, respectively, begin to increase by three times the retinal blood pressure values rP observed at lower stimulation pressure values SD $rPa_{VS}$: retinal arterial occlusion pressure Criterion: strong pulsations of the quotient signals or the red color intensity signals and the green color intensity signals, respectively, are no longer detectable and the quotient signals or the red color intensity signals and the green color intensity signals, respectively, have clearly increased over the values before the strong pulsations, by at least half the pulse amplitude $rP_{asys}$: retinal arterial systolic blood pressure Criterion: the strong arterial diameter pulsations have broken down to at least one third of half the diastolic pulse amplitude Step 3-4:

If the signal analysis unit 9 recognizes that at least one of the criteria for venous collapse is met, the resting intraocular pressure value $IOP_0$ is equated to the retinal venous blood pressure value rPv. In this case, the resting intraocular pressure value $IOP_0$ determines the retinal perfusion pressure value rPP on the venous side. Not only in this case, but also if the spontaneous venous collapse was not recognized, the computing and control unit 4 triggers the start of the unit for generating and applying a variable stimulation pressure 1 and the increase in variable stimulation pressure SD. The variable stimulation pressure SD is supposed to increase by at least 1 mmHg per second. See FIG. 5 for the time sequence below.

The signal analysis unit 9 continues to monitor the occurrence of measurement criteria. The computing and control unit 4 assigns all current stimulation pressure values SD to a time signal s(t), which is set to zero with the first start signal and to which all original and derived images of the video sequence, quotient images and signals are also assigned as of this point in time.

Step 3-5:

If the signal analysis unit 9 recognizes the spontaneous venous collapse on the optic nerve head, the computing and control unit 4 triggers the stop signal for the unit for generating and applying a variable stimulation pressure 1 and keeps the variable stimulation pressure SD constant. The computing and control unit 4 triggers an automatic tonometer measurement. The intraocular pressure value IOP measured at the stopping time is assigned to the time signal s(t). After storage and assignment of the intraocular pressure value IOP as a value for the retinal venous blood pressure outside the eyeball RVP, the increase in stimulation pressure is continued.

Step 3-6:

If another measurement criterion occurs, the computing and control unit 4 in turn triggers the stop signal for the unit for generating and applying a variable stimulation pressure 1, while the variable stimulation pressure SD is no longer increased and the associated intraocular pressure value IOP is determined by an automatic tonometer measurement triggered by the computing and control unit 4. The intraocular pressure value IOP is in turn assigned to the time signal s(t), but also to the measurement location or measurement locations in the retinal image and to the retinal blood pressure value rP associated with the measurement criterion.

If at least two tonometer measurements have been performed at different increased variable stimulation pressures SD, the individual correlation between the intraocular pressure values IOP in the eye A and the stimulation pressure values SD (IOP=f(SD)) is determined. Further intraocular pressure values IOP may be determined in order to increase the accuracy of this correlation. The correlation IOP=f(SD) is stored and may be used to compute any desired intraocular pressure values IOP from the current stimulation pressure values SD for the present examination.

Step 3-7:

Where measurement criteria occur for retinal arterial critical blood pressures $rPa_{krit}$ or retinal arterial occlusion pressures $rPa_{VS}$, the contiguous measurement locations on the retina are combined to measurement areas B or area elements and borderlines are formed for these measurement areas B. For each image containing these measurement areas B one retinal blood pressure value rP may be assigned and a dynamic representation of the critical or occluded measurement areas B may be presented. The development of these measurement areas B may also be summarized by color coding in a results image. Such a results image constituting a pressure mapping image is shown in FIG. 6c. The differently hatched measurement areas B, in which several measurement locations are respectively located, have different values, e. g. for retinal perfusion pressure rPP, retinal arterial critical blood pressure $rPa_{krit}$, or retinal arterial occlusion pressure $rPa_{VS}$.

Local retinal blood pressures rP, measured in vascular sections, may also be represented in a results image as a perfusion pressure and blood pressure mapping image (pressure mapping image), as shown in FIGS. 6a and 6b.

Step 3-8:

The examination is ended at the latest when reaching retinal suprasystolic blood pressure values rP, after determining the associated retinal arterial blood pressure rPa, and the computing and control unit 4 initiates a rapid decrease in variable stimulation pressure SD to 0. The measurement report and a pressure mapping image containing the acquire retinal blood pressure values rP, as well as a pressure mapping image containing the computed retinal perfusion pressure values rPP, are generated and output. The retinal blood pressure values rP and the retinal perfusion pressure values rPP may also be represented in a pressure mapping image.

Step 3-9:

Based on the local retinal arterial blood pressure values rPa, the local retinal perfusion pressure values rPP are then computed by approximative calculation from:

$$rPP.. = rPa.. - IOP0 (IOP0 > RVP) \text{ or}$$

$$rPP.. = rPa.. - RVP \text{ für } RVP > IOP0, \text{ respectively,}$$

and entered into the pressure mapping image for perfusion pressure mapping either directly or, for easier recognition, coded in different colors, e. g. red for retinal arterial occlusion pressures $rPa_{VS}$, yellow for retinal critical blood and perfusion pressures, and green for normal values of retinal blood pressure or perfusion pressure values.

Another advantageous embodiment may be the use of an imaging method on the basis of laser scanning technology by which normal images of the ocular fundus may be recorded or alternative embodiments of the invention are achieved by different-colored lasers, analogous to the described method on the basis of conventional retinal cameras.

Further alternative embodiments result if the imaging unit is embodied as an OCT device, i.e. imaging is effected on the basis of optical coherence tomatography. Based on the recorded OCT images, vascular signals are formed three-dimensionally and evaluated, as well as deriving signals which describe the local blood flow or local hematocrit (blood cell density) in the large retinal vessels or capillaries. As an example of this, OCT-A is used whose processed images describe the moving blood cell density (frequently also referred to as capillary density). Analogous to the previously described criteria, pulse changes or changes in the OCT signals, such as changes in local blood cell speed, local blood flow or the density of the moving blood cells, may be used as measurement criteria, which are then assigned to the blood pressure values defined above.

LIST OF REFERENCE NUMERALS 1 unit for generating and applying a variable stimulation pressure
1.1 pressure applicator
1.2 pressure generating unit
1.3 holder
2 imaging unit
3 tonometer
4 computing and control unit
5 input and output unit
6 digital video recorder
7 results storage unit
8 data and image evaluation unit
9 signal analysis unit
10 unit for generating spectral quotient signals
11 unit for generating vessel diameter signals
A eye
U examiner
B measurement area
s(t) time signal
rPP retinal perfusion pressure (value)
rP retinal blood pressure (value)
$rPa_{krit}$ retinal arterial critical blood pressure (value)
rPa retinal arterial blood pressure
rPv retinal venous blood pressure (value) (within the eyeball)
RVP retinal venous blood pressure (value) outside the eyeball
SD (variable) stimulation pressure (value)
IOP intraocular pressure (value)
$IOP_0$ resting intraocular pressure (value)
$rPa_{VS}$ retinal arterial occlusion pressure (value) (outside the eyeball)

What is claimed is:

1. A device comprising:
a unit for generating and applying a variable stimulation pressure (SD) acting on a patient's eye (A), the unit comprising a pressure applicator configured to be attached to a patient's head in a fixed manner with respect to the eye (A) in pressure-free planar contact with the eye (A);
a tonometer configured to measure automatically an intraocular pressure (IOP) in the eye (A), said intraocular pressure (IOP) changing as a function of the applied variable stimulation pressure (SD);
a first imaging unit; and
a computing and control unit having an input and output unit and being connected to the unit for generating and applying the variable stimulation pressure,
wherein the pressure applicator is configured to be attached to the patient's head outside the cornea and outside a light path of the first imaging unit,
wherein the tonometer and the first imaging unit are arranged for enabling measuring, by the tonometer the intraocular pressure (IOP) in the eye (A) while the stimulation pressure (SD) is applied and imaging by the first imaging unit at the same time; and wherein the tonometer is integrated in the first imaging unit, the tonometer being an automatically measuring rebound tonometer or a non-contact tonometer.

2. The device according to claim 1, wherein the unit for generating and applying the variable stimulation pressure is controllable such that the applied variable stimulation pressure (SD) is capable of changing direction, and varying speed can be increased or kept constant, and wherein the input and output unit is configured to effect control of the applied variable stimulation pressure (SD) by an examiner (U) via the input and output unit.

3. The device according to claim 2, wherein the first imaging unit comprises:
   a digital image sensor or a second imaging unit based on optical coherence tomography or on laser-scanning technology; and
   a digital video recorder connected to the digital image sensor or the second imaging unit and to the computing and control unit;
   wherein the input and output unit comprises a monitor and is configured such that the examiner (U) can either watch images from the digital image sensor or the second imaging unit online or video sequences of the images recorded by the digital video recorder to use for examination.

4. The device according to claim 3, further comprising a data and image evaluation unit in communication with the digital video recorder, the digital image sensor or the second imaging unit, the computing and control unit and the input and output unit;
   wherein the input and output unit is configured such that the examiner (U) can define measurement locations for detected visual measurement criteria in the images from the digital image sensor or the second imaging unit or the images of the video sequences which are displayed on the monitor, and wherein the input and output unit can store coordinates of the measurement locations together with the visual measurement criteria, each assigned to a respective retinal blood pressure value (rP), and enter the coordinates of the measurement locations and the respective retinal blood pressure value into a pressure mapping image.

5. The device according to claim 3, wherein the unit for generating and applying the variable stimulation pressure comprises a pressure sensor allowing a stimulation pressure value to be assigned to each value of the measured intraocular pressure (IOP) or to each image of the video sequence, respectively.

6. The device according to claim 1, further comprising a unit for generating vessel diameter signals which is configured to generate, for each vascular segment, a vessel diameter signal correlating with a diameter and assign said signal to a time signal (s(t)) of the computing and control unit.

7. A method for determining retinal blood pressure values in a patient's eye (A), the method comprising:
   applying a variable stimulation pressure (SD) to the eye (A), causing changing of an intraocular pressure in the eye (A) as a function of the applied variable stimulation pressure (SD);
   observing the retina of the eye and/or recording a video sequence of images of the retina of the eye simultaneously with the applying the variable stimulation pressure (SD) to the eye (A);
   measuring a current intraocular pressure value by automatically using a tonometer;
   equating the current intraocular pressure value to one of the retinal blood pressure values if compliance with a characteristic measurement criterion for said one retinal blood pressure value is observed on the retina or derived from the images;
   keeping constant the variable stimulation pressure (SD) over a period of time when the compliance with the characteristic measurement criterion in at least one point in time is observed;
   performing a direct measurement of the intraocular pressure during said period of time of keeping constant the variable stimulation pressure (SD) by automatically using the tonometer;
   directly equating the direct measurement of the intraocular pressure to that one of the retinal blood pressure values for which said characteristic measurement criterion was met;
   obtaining a local retinal perfusion pressure value from the one of the retinal blood pressure values when the one of the retinal blood pressure values is a local retinal arterial blood pressure value, wherein the local retinal perfusion pressure value is obtained by calculating a difference between the local retinal arterial blood pressure value and a resting intraocular pressure value or a retinal venous blood pressure value outside the eyeball;
   representing the local perfusion pressure value in a pressure mapping image
   deriving illumination-independent spectrally normalized signals from the images of the video sequence and assigning the illumination-independent spectrally normalized signals to a point in time and a measurement location; and
   assigning a rise and fall of vascular pulsations, pulsatory and continuous pallor, or signal changes as further characteristic measurement criteria and/or assigning the global and/or local retinal blood pressure values as threshold values to the illumination-independent spectrally normalized signals; and
   using the further characteristic measurement criteria and/or the threshold values to automatically measure or determine the intraocular pressure.

8. The method according to claim 7, further comprising generating a time signal (s(t)) and assigning to the time signal (s(t)) the measured intraocular pressure value, stimulation pressure values, the images of the retina and/or the images of the video sequence, points in time of occurrence of characteristic measurement criteria, and respective retinal blood pressure values.

9. The method according to claim 8, further comprising using at least two directly measured intraocular pressure values and the stimulation pressure values respectively assigned via the time signal (s(t)) to compute, for the monitored patient's eye (A), an individual correlation between one of the intraocular pressure values and one of the stimulation pressure values, wherein in a case when only one intraocular pressure value has been measured directly upon occurrence of one of the characteristic measurement criteria, a further intraocular pressure value is measured directly at any point in time during an elevated portion of the stimulation pressure values, without occurrence of one of the characteristic measurement criteria.

10. The method according to claim 9, further comprising:
   deriving occurrences of the characteristic measurement criteria of the global retinal blood pressure values by an examiner (U) during the recording of the video sequence from the images online;

based on the video sequence, interactively marking, temporally, the occurrences of the characteristic measurement criteria of local retinal blood pressures (rP) offline in measurement locations in the images;

determining respective intraocular pressure values for each of the occurrences via the time signal (s(t)), and equating each of the respective intraocular pressure values to a respective retinal blood pressure value; and storing the retinal blood pressure values (rP) and the respective measurement locations and entering them in the pressure mapping image.

11. The method according to claim 9, further comprising deriving vessel diameter signals from the images of the video sequence and assigning each of the vessel diameter signals to a respective point in time and to a vascular segment or to a vascular section comprising vascular segments.

12. The method according to claim 7, further comprising detecting the characteristic measurement criteria over the entire retina, deriving therefrom retinal regions representing pathological vascular regions that can be considered when analyzing a vascular risk of retinal circulation problems in individual capillary regions.

13. The method according to claim 12, wherein measurement locations or vascular segments in which the same measurement criteria occur at the same time are combined with vascular sections or vascular regions and assembled in the pressure mapping image, and wherein different retinal blood pressure values and/or measurement criteria are presented in a color-coded manner.

* * * * *